(12) United States Patent
Buijs et al.

(10) Patent No.: US 10,832,854 B2
(45) Date of Patent: Nov. 10, 2020

(54) DISSOLVED GAS ANALYSIS DEVICES, SYSTEMS, AND METHODS

(71) Applicant: ABB Schweiz AG, Baden (CH)

(72) Inventors: Henry L. Buijs, Quebec (CA); Louis-Philippe A. Bibeau, Saint-Augustin-de-Desmaures (CA); Alex Ouellet-Belanger, Boischatel (CA); Raphael N. Desbiens, Quebec (CA)

(73) Assignee: ABB Schweiz AG, Baden (CH)

( * ) Notice: Subject to any disclaimer, the term of this patent is extended or adjusted under 35 U.S.C. 154(b) by 0 days.

(21) Appl. No.: 16/814,485

(22) Filed: Mar. 10, 2020

(65) Prior Publication Data
US 2020/0211761 A1    Jul. 2, 2020

Related U.S. Application Data

(62) Division of application No. 15/458,010, filed on Mar. 13, 2017, now Pat. No. 10,586,649, and a division of
(Continued)

(51) Int. Cl.
| | |
|---|---|
| *H01F 27/12* | (2006.01) |
| *H01F 27/28* | (2006.01) |
| *H01F 27/40* | (2006.01) |
| *G01N 1/22* | (2006.01) |
| *G01N 33/28* | (2006.01) |
| *G01N 21/35* | (2014.01) |
| *G01N 21/65* | (2006.01) |
| *G01N 21/39* | (2006.01) |

(52) U.S. Cl.
CPC ....... *H01F 27/2876* (2013.01); *G01N 1/2205* (2013.01); *G01N 1/2226* (2013.01); *G01N 33/2841* (2013.01); *H01F 27/12* (2013.01); *H01F 27/402* (2013.01); *G01N 21/65* (2013.01); *G01N 2001/2267* (2013.01); *G01N 2021/3595* (2013.01); *G01N 2021/399* (2013.01)

(58) Field of Classification Search
CPC ............... H01F 27/00–40; G01N 7/00; G01N 2001/2267; G01N 33/2841
USPC .................................. 336/55–62; 73/19, 23
See application file for complete search history.

(56) References Cited

U.S. PATENT DOCUMENTS

| | | | | |
|---|---|---|---|---|
| 2,340,898 A | * | 2/1944 | Race ....................... | H01F 27/14 174/14 R |
| 3,844,160 A | * | 10/1974 | Yamaoka ........... | G01N 33/2841 73/19.11 |

(Continued)

FOREIGN PATENT DOCUMENTS

| | | |
|---|---|---|
| EP | 1950560 A1 | 7/2008 |
| ES | 2440893 A2 | 1/2014 |

(Continued)

OTHER PUBLICATIONS

International Search Report for PCT/CA2018/050298 dated May 24, 2018, 9 pages.

(Continued)

*Primary Examiner* — Tuyen T Nguyen
(74) *Attorney, Agent, or Firm* — Barnes & Thornburg LLP (57) ABSTRACT

Devices, systems, and methods for determining gas characteristics to monitor transformer operation include extracting gas from transformer fluid for analysis.

20 Claims, 6 Drawing Sheets

Related U.S. Application Data application No. 15/458,014, filed on Mar. 13, 2017, now Pat. No. 10,585,036.

(56) References Cited

U.S. PATENT DOCUMENTS

| | | | |
|---|---|---|---|
| 4,112,737 A | 9/1978 | Morgan | |
| 4,409,814 A * | 10/1983 | Onuma | G01N 33/2841 73/19.02 |
| 5,246,868 A | 9/1993 | Busch et al. | |
| 5,473,162 A | 12/1995 | Busch et al. | |
| 5,811,812 A | 9/1998 | Williams et al. | |
| 6,037,592 A | 3/2000 | Sunshine et al. | |
| 6,324,891 B1 | 12/2001 | Gibeault et al. | |
| 6,391,096 B1 * | 5/2002 | Waters | B01D 19/0031 73/19.02 |
| 6,526,805 B1 | 3/2003 | Babes-Dornea et al. | |
| 6,610,982 B2 | 8/2003 | Hoult | |
| 7,040,138 B2 * | 5/2006 | Braesel | G01N 33/2841 73/19.01 |
| 8,014,965 B2 | 9/2011 | Desbiens et al. | |
| 8,442,775 B2 | 5/2013 | Santos | |
| 10,429,371 B2 * | 10/2019 | Virtanen | B01F 3/04503 |
| 10,585,036 B2 | 3/2020 | Buijs et al. | |
| 10,586,649 B2 | 3/2020 | Buijs et al. | |
| 2012/0306656 A1 | 12/2012 | Boucher et al. | |
| 2016/0266085 A1 | 9/2016 | Hollunder et al. | |
| 2018/0259444 A1 | 9/2018 | Buijs et al. | |
| 2018/0259451 A1 | 9/2018 | Buijs et al. | |

FOREIGN PATENT DOCUMENTS

| | | |
|---|---|---|
| JP | 2-285257 A | 11/1990 |
| JP | 2000275150 A | 10/2000 |
| JP | 2010-8175 A | 1/2010 |
| WO | 1998/020324 A1 | 5/1998 |
| WO | 2013/116799 A1 | 8/2013 |

OTHER PUBLICATIONS

Teflon AF Overview, Professional Plastics, 5 pages.
USPTO, Office Action concerning U.S. Appl. No. 15/458,010, dated Sep. 17, 2019, 6 pages.
USPTO, Non-Final Office Action concerning U.S. Appl. No. 15/458,014, dated Aug. 16, 2019, 13 pages.

* cited by examiner

DISSOLVED GAS ANALYSIS DEVICES, SYSTEMS, AND METHODS

CROSS-REFERENCE TO RELATED APPLICATIONS

This application is a divisional of U.S. patent application Ser. No. 15/458,010, filed Mar. 13, 2017, now U.S. Pat. No. 10,586,649, the entire disclosure of which is incorporated herein by reference. This application is also a divisional of U.S. patent application Ser. No. 15/458,014, filed Mar. 13, 2017, now U.S. Pat. No. 10,585,036, the entire disclosure of which is incorporated herein by reference.

TECHNICAL FIELD

The present disclosure relates to the field of dissolved gas analysis. More particularly, the present disclosure relates to dissolved gas analysis for transformers.

BACKGROUND

Electromagnetic devices, such as electrical transformers, can experience electrical inefficiencies and can generate significant heat in operation. Abating electrical inefficiencies and removing excess heat from such devices can conserve operational life, performance, and reduce the maintenance needs of the devices. Fluids, such as dielectric fluids, can be used as a cooling medium to remove heat from the devices and can provide an electrical insulation layer to suppress corona and arcing.

In operation, such cooling and/or insulating fluids can develop dissolved gases. Analysis of dissolved gases within the fluids of transformers can reveal useful information regarding the status of transformer operation.

SUMMARY

According to an aspect of the present disclosure, a gas analysis system for determining characteristics of gas dissolved in a fluid of a transformer may include an extraction coil for contact with the fluid, the extraction coil including gas-permeable material for receiving dissolved gas, a gas analyzer for determining gas characteristics, the gas analyzer including a gas cell having a cavity for receiving gas for analysis, and a gas circuit formed to include the extraction coil and the gas analyzer to circulate gas.

In some embodiments, the extraction coil may include a number of coil loops each permitting dissolved gas to permeate therein. The gas circuit may include a transport conduit fluidly coupled with each of the extraction coil and the gas analyzer to transport gas between the extraction coil and the gas cell for analysis. In some embodiments, the transport conduit may include a motive pressure source fluidly coupled with the extraction coil to circulate gas through the transport conduit.

In some embodiments, the motive pressure source may be fluidly coupled with the extraction coil to provide a lower pressure within the extraction loop relative to a pressure within the cavity of the gas cell. In some embodiments, the transport conduit may include a supply segment fluidly connected to provide gas from the extraction loop to the gas cell. In some embodiments, the transport conduit may include a return segment fluidly connected to provide gas from the gas cell to the extraction loop.

In some embodiments, the gas analyzer may include a light source and at least one light detector for receiving light from the light source. In some embodiments, the light source may be arranged to pass light from one side of the gas cell through gas within the cavity of the gas cell to another side of the gas cell, and the at least one light detector may be arranged on the another side to receive light from the light source. In some embodiments, the cavity of the gas cell may be arranged for receiving dissolved gas extracted from the fluid.

In some embodiments, the gas-permeable material may include a fluoropolymer. In some embodiments, the gas-permeable material may include a fluoroplastic having at least one of: a yield strength within the range of about 26 MPa to about 29 MPa at about 73° F., a yield strength within the range of about 0.5 MPa to about 13 MPa at about 302° F., a yield strength within the range of about 4 MPa to about 13 MPa at about 428° F., a tensile strength within the range of about 24 MPa to about 29 MPa at about 73° F., a tensile strength within the range of about 1 MPa to about 15 MPa at about 302° F., and a tensile strength within the range of about 3 MPa to about 7 MPa at about 428° F. In some embodiments, the fluoropolymer may include a fluoroplastic having optical transmission percent of greater than 95. In some embodiments, the fluroplastic may include a fluoroplastic having gas permeability of at least one of $H_2O$ of about 1142 Barrer, $O_2$ of about 340 Barrer, and $N_2$ of about 130 Barrer.

In some embodiments, the extraction coil may be formed as a conduit having an inner volume for receiving gas permeating through the gas-permeable material. In some embodiments, a gas species that is both within the inner volume and dissolved in the fluid may be in equilibrium.

According to another aspect of the present disclosure, a transformer may include at least one electrical winding, a fluid system including fluid for insulating the at least one electrical winding, and a gas analysis system for determining characteristics of gas dissolved in the fluid of the fluid system. In some embodiments, the gas analysis system may include an extraction coil and a gas cell for analysis of gas, and the extraction coil may be arranged in contact with the fluid and including a gas-permeable material for receiving dissolved gas from the fluid, the extraction coil and the gas cell fluidly communicating to form a gas circulation loop for circulating gas.

In some embodiments, the gas cell may be arranged for determining characteristics of gas extracted from the fluid. In some embodiments, a transport conduit may be fluidly coupled with each of the extraction coil and the gas cell to transport gas received from the fluid to the gas cell for analysis. In some embodiments, the extraction coil may be formed as a conduit having an inner volume for receiving gas permeating through the gas-permeable material. In some embodiments, a gas species that is both within the inner volume and dissolved in the fluid may be in equilibrium.

In some embodiments, the gas-permeable material may include a fluoropolymer. In some embodiments, the gas-permeable material may include a fluoroplastic having at least one of: a yield strength within the range of about 26 MPa to about 29 MPa at about 73° F., a yield strength within the range of about 0.5 MPa to about 13 MPa at about 302° F., a yield strength within the range of about 4 MPa to about 13 MPa at about 428° F., a tensile strength within the range of about 24 MPa to about 29 MPa at about 73° F., a tensile strength within the range of about 1 MPa to about 15 MPa at about 302° F., and a tensile strength within the range of about 3 MPa to about 7 MPa at about 428° F. In some embodiments, the fluoropolymer may include a fluoroplastic having optical transmission percent of greater than 95. In some embodiments, the fluroplastic may include a fluoroplastic having gas permeability of at least one of $H_2O$ of about 1142 Barrer, $O_2$ of about 340 Barrer, and $N_2$ of about 130 Barrer.

According to another aspect of the present disclosure, a gas analysis device for determining characteristics of dissolved gas of a transformer may include a gas cell defining a cavity for receiving gas for analysis, a light source arranged to transmit light, a cell light detector arranged to receive light propagated by the light source through the cavity of the gas cell, and a reference light detector arranged to receive light propagated by the light source through an ambient space.

In some embodiments, a cell light distance is defined between the cell light source and a reference source point of light from the light source. In some embodiments, the cell light distance may correspond to a reference light distance defined between the reference source point and the reference light detector. In some embodiments, the reference source point may be a beam splitter arranged to divide light from the light source into at least two beams, one of the at least two beams for propagation through the cavity and another of the at least two beams for propagation through the ambient space.

In some embodiments, the cell light detector may be arranged to receive light from the beam propagated through the cavity that has not been absorbed by gas within the cavity, and wherein the reference light detector may be arranged to receive light from the beam propagated through the ambient space that has not been absorbed by gas within the ambient space. In some embodiments, each of the cell light detector and the reference light detector may provide a signal indicating a spectrum corresponding to light received by that detector.

According to another aspect of the present disclosure, a transformer may include at least one electrical winding, a fluid system including fluid for insulating the at least one electrical winding, and a gas analysis system for determining characteristics of gas dissolved in the fluid of the fluid system, the gas analysis system including an extraction probe having gas-permeable material for receiving dissolved gas from the fluid and a gas analyzer including at least two channels. In some embodiments, at least one of the at least two channels may be arranged to determine characteristics of gas extracted from the fluid.

In some embodiments, at least one of the two channels may be arranged to determine characteristics of ambient gas. In some embodiments, the at least two channels may be arranged to receive light propagated from the same light source.

In some embodiments, the at least one channel may be arranged to propagate light through a gas cell containing gas extracted from the fluid for reception by a cell detector of the at least one channel. In some embodiments, a cell light distance may be defined between a reference source point of light of the light source and the cell detector. In some embodiments, the cell light distance may correspond to a reference light distance defined between the reference source point and a reference detector of at least one other channel of the at least two channels.

In some embodiments, the reference source point may include a beam splitter arranged to divide light from the light source into at least two beams, one of the at least two beams for propagation through the gas cell and another of the at least two beams for propagation through ambient space. In some embodiments, the cell light detector may be arranged to receive light from the beam propagated through the gas cell that has not been absorbed by gas within the gas cell, and wherein the reference light detector is arranged to receive light from the beam propagated through the ambient space that has not been absorbed by gas within the ambient space.

In some embodiments, each of the cell detector and the reference detector may provide a signal indicating a spectrum corresponding to light received by that detector.

In some embodiments, the gas analyzer may include a gas cell fluidly connected with the extraction probe to form a gas circuit. In some embodiments, the extraction probe may include an extraction coil. In some embodiments, the extraction coil may include a number of coil turns arranged in contact with the fluid.

According to another aspect of the present disclosure, a transformer may include at least one electrical winding, a transformer fluid system including fluid for insulating the at least one electrical winding, a gas analysis system for determining characteristics of gas dissolved in the fluid of the fluid system, the gas analysis system including an extraction probe having gas-permeable material for receiving dissolved gas from the fluid and a gas analyzer including at least two channels. In some embodiments, at least one of the at least two channels may be arranged to determine characteristics of gas received from the fluid. In some embodiments, a gas circuit may be defined at least partially by the extraction probe and the gas analyzer for circulating gas extracted from the fluid.

In some embodiments, the gas analyzer may include a gas cell fluidly connected with the extraction probe to form the gas circuit. In some embodiments, the gas analyzer may propagate light through gas within the gas cell for reception by a detector of the at least one channel.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements. The detailed description particularly refers to the accompanying figures in which.

DETAILED DESCRIPTION OF THE DRAWINGS

While the concepts of the present disclosure are susceptible to various modifications and alternative forms, specific embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Figure 1:
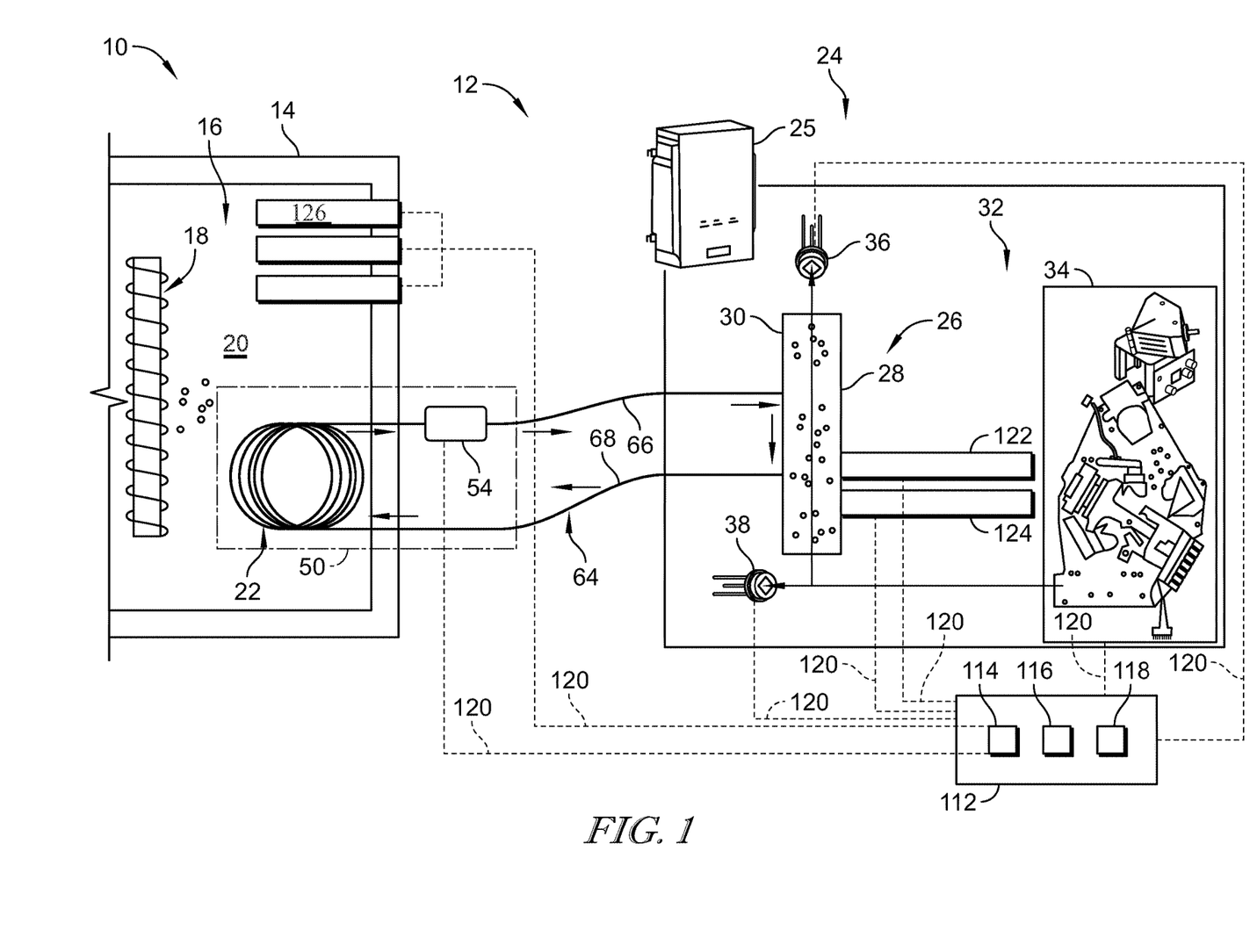
FIG. 1 is a diagrammatic view of an electrical transformer showing that the transformer includes a gas analysis system for determining characteristics of dissolved gases within fluid of the transformer, and that the gas analysis system includes a gas-permeable extraction probe for extracting gases from the fluid and a gas analysis module for performing analysis on the extracted gas, and showing that the extraction probe and the analysis module are fluidly connected to form a gas circuit.

FIG. 1 shows an illustrative arrangement of an electrical transformer 10 including a gas analysis system 12 for determining characteristics of dissolved gases within fluid of the transformer 10. The transformer 10 illustratively includes a housing 14 defining an interior 16 and electrical windings 18 arranged within the interior 16 of the housing 14. The electrical windings 18 illustratively comprise windings of electrical wiring forming a series of turns about limbs of the transformer 10 to produce electromagnetic effect when current is passed through the wiring. The transformer 10 is illustratively embodied as a high-voltage, three-phase, core type transformer, but in some embodiments, may include any manner of electromagnetic device including but not limited to shell type and/or single or multi-phase.

In the illustrative embodiment as shown in FIG. 1, the housing 14 contains fluid 20 for cooling and/or electrically insulating the components of the transformer 10, such as the electrical windings 18. As mentioned above, dissolved gases can develop within the fluid 20 as a result of operable use of the fluid 20 for cooling and/or insulation (for example, by fluid breakdown and/or faulty operational issues of the transformer 10, generally, including leaks in the housing 14) and/or the fluid 20 may carry gases generated from the degradation of other insulation materials in the transformer, such as paper. The gas analysis system 12 is illustratively arranged to extract dissolved gases from the fluid 20 for analysis.

Referring to FIG. 1, the gas analysis system 12 illustratively includes an extraction probe 22 for extracting gas from the fluid 20. The extraction probe 22 is illustratively arranged in contact with the fluid 20 and is formed of a gas-permeable material to permit permeation of dissolved gases from the fluid 20. The extraction probe 22 is illustratively embodied as a conduit defining an interior passage for receiving and communicating gas. The gas-permeable material illustratively permits dissolved gases to permeate into the interior passage while inhibiting ingress of liquids, for example, dielectric oils. Suitable gas-permeable materials may include one or more fluoropolymers. In the illustrative embodiment, the extraction probe 22 is formed as an extraction coil having coil loops in contact with the fluid 20. In some embodiments, the extraction probe 22 may include any suitable shapes and/or forms.

As shown in FIG. 1, the gas analysis system 12 illustratively includes a gas analysis module 24 for conducting analysis of gas. The gas analysis module 24 is illustratively fluidly connected with the extraction probe 22 and forms a gas circuit for circulation of gas between the extraction probe 22 and the gas analysis module 24. An exemplary housing 25 of the gas analysis module 24 is shown in FIG. 1. The gas analysis module 24 illustratively includes a gas cell 26 for receiving gas extracted from the fluid 20. The gas cell 26 illustratively includes a cell body 28 defining a cavity 30 through which gas is passed for analysis. In the illustrative embodiment, the gas analysis system 12 conducts optical analysis of gas to determine gas characteristics. In the illustrative embodiment, portions of the gas circuit other than the extraction probe 22, including the cavity 30, are hermetically sealed to ambient air such that only the extraction probe 22 is arranged to allow permeation of gases into and out of the gas circuit, thereby allowing gas exchange with the transformer fluid 20.

As shown in FIG. 1, the gas analysis module 24 illustratively includes a gas analysis device 32 for conducting analysis of gas within the gas cell 26. In the illustrative embodiment, the gas analysis device 32 is an optical device embodied as a light spectroscopy device, namely a Fourier transform infrared (FTIR) spectrometer. In some embodiments, the gas analysis module 24 may perform any manner of gas analysis techniques and may include any suitable configuration and/or components to perform such techniques, for example, but without limitation, ultra violet light spectroscopy, Raman spectroscopy, photoacoustic spectroscopy, tunable diode laser absorption spectroscopy (TDLAS). The gas analysis device 32 illustratively performs light spectrum analysis of gas within the gas cell 26. In some embodiments, the gas cell 26 may use optical path length enhancement techniques such as multi-pass cells or resonant cavities. Multi-pass cells may include White cell, Herriot cell, folded path cells, and/or other multi-pass cells. Resonant cavities may include Fabry-Perot cavities, cavities designed for cavity ring-down spectroscopy, integrated cavity output spectroscopy (ICOS), off-axis integrated cavity output spectroscopy (OA-ICOS), and/or other optical path length enhancement techniques.

As shown in FIG. 1, the gas analysis device 32 illustratively includes a light source 34 and detectors 36, 38 for receiving light from the light source 34. As discussed in additional detail below, the light source 34 illustratively generates infrared (IR) light for propagation through gas for observation of the light absorption characteristics of the gas. The light directed through the gas is received by the detectors 36, 38. The detectors 36, 38 are illustratively embodied as photodetectors that receive light propagated through gas (but that has not been absorbed by the gas) and that generate an electrical signal indicating the light received. The detectors 36, 38 are illustratively embodied as analog detectors that generate an analog signal that is converted to a digital signal by an analog-to-digital converter. In some embodiments, the detectors 36, 38 may include any suitable arrangement of signal generation for gas analysis.

The gas analysis device 32 illustratively determines characteristics of the gas based on the light received by the detectors 36, 38. In the illustrative embodiments, the gas analysis module 24 can determine characteristics of dissolved gas within the fluid 20 by analysis of gas extracted by the gas analysis system 12 from the transformer 10. Relevant characteristics of dissolved gases within the fluid 20 f the transformer 10 include the presence and/or identification of such gases and their dissolved concentrations within the fluid 20. A non-exhaustive list of gases of interest within the fluid 20 may include, for example, oxygen ($O_2$), nitrogen ($N_2$), hydrogen ($H_2$), carbon dioxide ($CO_2$), and/or hydrocarbons (e.g., methane, ethane, acetylene, and/or ethylene), among other gases. The gas analysis device 32 may also monitor water vapor ($H_2O$) extracted from the moisture dissolved in transformer oil 20.

Figure 2:
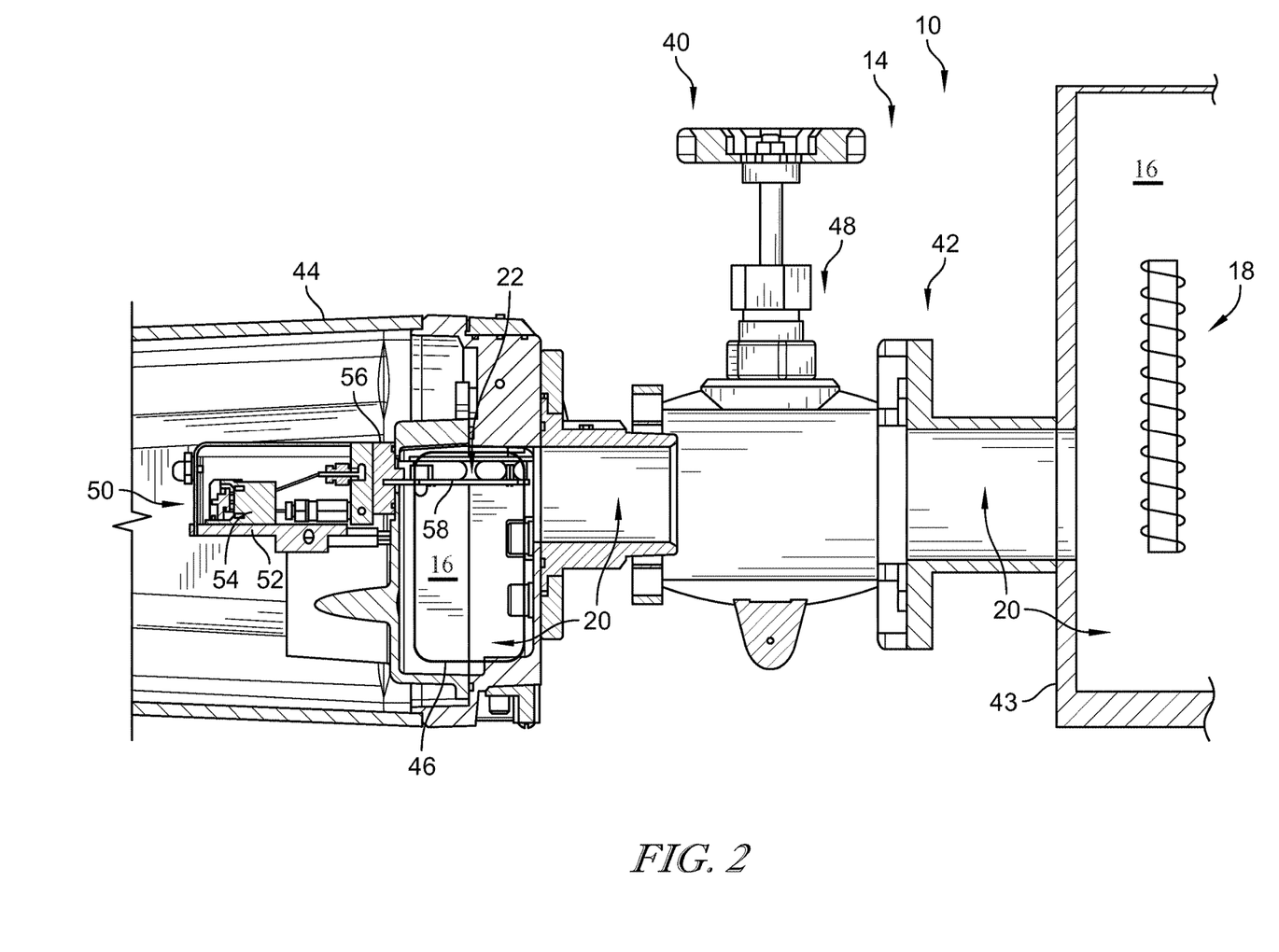
FIG. 2 is an elevation view of an illustrative embodiment of a sample portal of the electrical transformer of FIG. 1 in partial cross-section to show that an extraction module including the extraction probe is arranged to place the extraction probe in contact with the fluid of the transformer.

Referring now to FIG. 2, the transformer 10 is shown in partial cross-section for descriptive purposes. The housing 14 of the transformer 10 illustratively includes a sampling portal 40 defining a portion of the interior 16 containing fluid 20 as part of the housing 14. The sampling portal 40 illustratively includes pipe extension 42 connected with a wall 43 of the transformer 10 and a shroud 44 secured with the pipe extension 42. The extraction probe 22 is illustratively mounted within the shroud 44 in contact with fluid 20. The extraction probe 22 is illustratively mounted within a fluid chamber 46 defined by the shroud 44 as a part of the interior 16. The chamber 46 illustratively contains fluid 20 as part of the housing 14 and fluidly communicating through the pipe extension 42. In the illustrative embodiment, the pipe extension 42 illustratively includes a valve 48 disposed fluidly between the wall 43 and the chamber 46 to permit isolation of the extraction probe 22, but in some embodiments, the valve 48 may be excluded. In some embodiments, the extraction probe 22 may be arranged inside of the wall 43.

Figure 3:
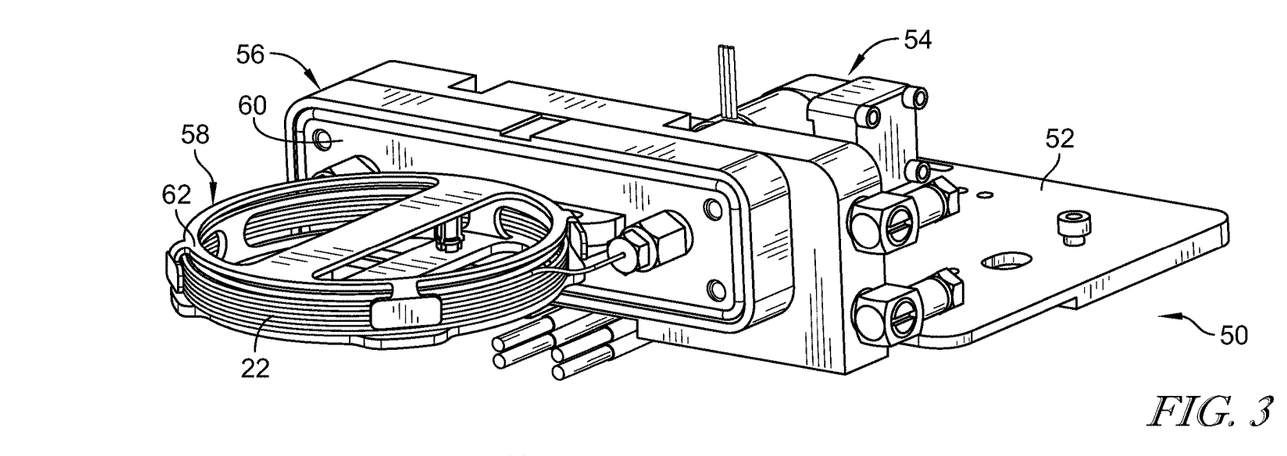
FIG. 3 is a perspective view of an illustrative embodiment of the extraction module showing that the extraction probe is mounted on a frame to form the extraction module.
Figure 4:
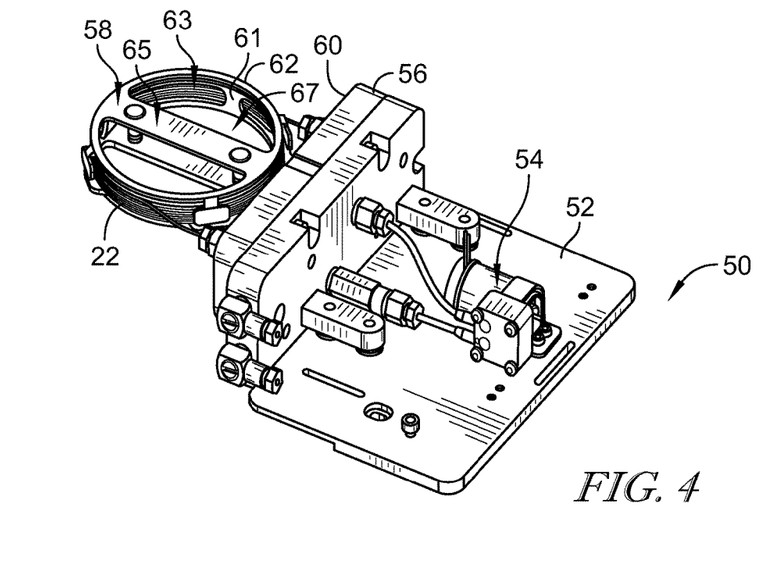
FIG. 4 is another perspective view of the extraction module of FIG. 3 showing that the extraction probe is formed as an extraction coil and is mounted on a spool of the frame.

The gas analysis system 12 illustratively includes an extraction module 50 as shown in FIGS. 2-4. The extraction module 50 illustratively provides a packaging platform for mounting the extraction probe 22 within the housing 14 as shown in FIG. 2. Referring to FIGS. 3 and 4, the extraction module 50 illustratively includes a mounting frame 52 and the extraction probe 22 secured with the mounting frame 52. In the illustrative embodiment, a pump 54 is mounted to the frame 54 and is fluidly connected with the extraction probe 22 to provide a motive pressure source for circulation of gas within the gas circuit. Control valves and/or other flow distribution devices for operation of the gas circuit may be mounted to the mounting frame 52.

As shown in FIGS. 3 and 4, the mounting frame 52 illustratively includes an engagement wall 56 and a probe arm 58 extending from the engagement wall 56. The engagement wall 56 illustratively includes a face 60 that forms at least a portion of fluid boundary of the chamber 46. The engagement wall 56 illustratively supports the probe arm 58 for extension within the chamber 46 for contact with fluid 20.

In the illustrative embodiment as shown in FIGS. 3 and 4, the probe arm 58 includes a spool 62 having the extraction probe 22 (embodied as an extraction coil) looped around the spool 62. In the illustrative embodiment, the extraction coil is looped around the spool 62 to form a number of coil turns having a successively stacked arrangement for exposure to fluid 20. Increasing the number of coils may improve the effective exchange surface between oil and gas phase and may reduce the response time of the measurement. Gas circulated through the extraction probe 22 portion of the gas circuit illustratively flows successively through each of the coil turns and out for circulation to the gas analysis device 32. In the illustrative embodiment, the extraction probe 22 is fluidly connected with the pump 54 for communication of extracted gas through the gas circuit.

As best shown in FIG. 4, the spool 62 is illustratively cantilevered from the engagement wall 56 and provides structure for arranging the extraction probe 22 for contact with fluid 20. In some embodiments, the extraction probe 22 may be secured to the mounting frame 52 in any suitable manner and/or arrangement. The spool 62 is illustratively formed as a structural frame defining an annular spool bed 61 for receiving the extraction probe 22 wrapped thereon and defining openings 63 extending through the spool bed 61 to permit fluid 20 to contact interior portions of the extraction probe 22 to increase the effective exchange surface between oil and gas phase. The spool 62 is illustratively shaped as a hollow cylinder to permit fluid 20 therein. The spool 62 illustratively includes a strut 65 bridging radially across the spool bed 61 to provide structural support and defining openings 67 to permit circulation of fluid 20 through the spool 62.

Returning briefly to FIG. 1, as previously mentioned, the extraction probe 22 and the gas analysis module 24 are fluidly connected to define a gas circuit for circulation of gas therebetween. In the illustrative embodiment, the extraction probe 22 and the gas analysis module 24 are fluidly connected by transport conduit 64 including conduit segments 66, 68. The segment 66 is illustratively embodied as a supply segment for providing gas from the extraction probe 22 to the gas analysis module 24 and the segment 68 is embodied as a return segment for providing gas from the gas analysis module 24 to the extraction probe 22.

In the illustrative embodiment, the pump 54 is arranged fluidly along the supply segment 66 and provides a lower pressure level at the output of the extraction probe 22 (relative to the pressure of the gas cell 26), which may assist with extraction of dissolved gases. In some embodiments, the gas circuit may be formed substantially or entirely by the extraction probe 22 and gas analysis module 24 being fluidly connected with each other by direct connection and/or with little or no transport conduit 64. In some embodiments, the extraction probe 22 and gas analysis module 24 may be partly or wholly combined into a common module and/or arranged within a common housing for compact arrangement.

The gas circuit illustratively provides a circulation loop for communication of gas between the extraction probe 22 and the gas analysis module 24. In the illustrative embodiment, the gas circuit encourages the gas extracted from the fluid 20 to reach and maintain equilibrium with dissolved gases within the fluid 20. Such passive extraction and non-destructive analysis can avoid practical challenges with active sampling, such as fluid leaks, contamination, and waste materials, among others. Passive extraction does not rely on a precise determination of the extraction rate of the gas and thus reduces the need for factory calibration of each analyzer extraction rate. As mentioned above, the pump 54 illustratively assists circulation of the gas through the gas circuit and may assist extraction, but in some embodiments, circulation of the gas through the gas circuit may be provided by any suitable device(s), including but not limited to redundant pumps arrangements or arrangements without a pump such as convective and/or diffusive transport.

Figure 5:
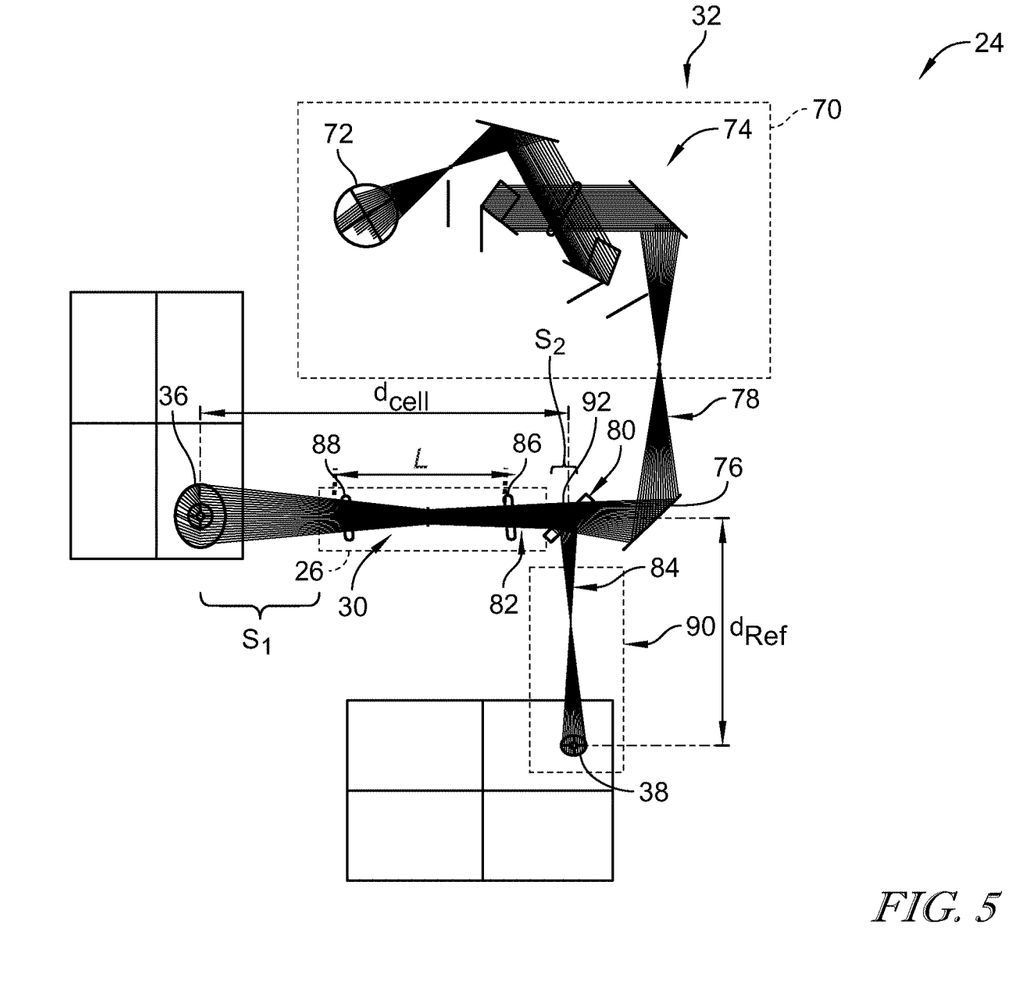
FIG. 5 is a diagrammatic view of the gas analysis module showing that the gas analysis module includes a gas cell containing extracted gases and a reference space containing ambient gases, and showing that the gas analysis module includes a light source providing a first channel for measuring gas within the gas cell by passing a first light beam through the gas cell for reception by a first detector, and a second channel for measuring gas within the reference space by passing a second light beam through the reference space for reception by a second detector.

Referring now to FIG. 5, a diagrammatic illustration of the gas analysis module 24 is shown. As mentioned above, the gas analysis module 24 illustratively includes the gas analysis device 32 arranged for conducting analysis of gas within the gas cell 26. The light source 34 of the gas analysis device 32 illustratively includes a light generation source 70. In the illustrative embodiment, the light generation source 70 includes an interferometer for modulating mid-IR light, for example, with a wavelength within a range of about 1 microns to about 50 microns (in some illustrative embodiments), about 2.5 microns to about 25 microns (in other illustrative embodiments), and about 2.5 to about 16 microns (in still other illustrative embodiments). The light generation source 70 also illustratively includes at least one light generator 72 for generating the mid-IR light and may include various relays, filters, and/or other conditioning devices (collectively indicated as 74) for providing suitable light for gas analysis. A non-limiting example of a suitable light generator 72 may include a glow bar (globar). The light source 34 illustratively includes a relay mirror 76 arranged to receive a beam of light 78 from the light generation source 70 and a beam splitter 80 arranged to receive the beam 78 from the relay mirror 76.

As shown in FIG. 5, the gas analysis device 32 illustratively includes two optical channels as explained herein. The beam splitter 80 illustratively divides the beam 78 into two beams of light 82, 84 for spectrum analysis. The beam splitter 80 is illustratively embodied to have a beam-splitting ratio of 50:50 (50/50 splitter) dividing the beam 78 evenly into the two beams 82, 84, but in some embodiments, the beam splitter 80 may have other suitable beam-splitting ratios. In some embodiments, any suitable arrangement of relays, filters, splitters, and/or other conditioning devices may be employed to propagate light accordingly for gas analysis. Beams 82, 84 propagate through respective defined spaces for collection by detectors 36, 38.

In the illustrative embodiment as shown in FIG. 4, analysis of the beams 82, 84 propagated through respective defined spaces can determine characteristics of the gas extracted from the fluid 20. The beam 82 illustratively propagates through the gas cell 26 for reception by detector 36. The beam 82 illustratively enters the gas cell 26 through a window 86, propagates through the cavity 30 for interaction with gas therein, and exits the gas cell 26 through another window 88. Light from the beam 82 exiting the gas cell 26 is received by the detector 36 for analysis. The gas within the cavity 30 affects the beam 82 in a manner such that the affected light received by detector 36 can indicate characteristics of the gas within the cavity 30. As explained below, the detector 36 can generate a signal related to the absorption spectrum of the gas within the cavity 30 based on the light received from beam 82.

In the illustrative embodiment, the gas within the cavity 30 absorbs energy from the beam 82 in the form of electromagnetic radiation. The remaining energy of beam 82 passes through the gas and is received by the detector 36 to generate a signal related to an absorption spectrum in the illustrative embodiment. The absorption spectrum of the relevant gas can include the fraction of incident radiation absorbed by the gas sample (in this instance, the gas within the cavity 30) over a range of wavelengths and/or frequencies of propagated light. By analysis of the light received by the detector 36 (for example, but without limitation, the wavelength and/or frequency thereof), the characteristics of the gas within the cavity 30 can be reliably determined. Moreover, characteristics of the dissolved gases within fluid 20 can be determined based on the characteristics of the gas within the cavity 30. In some embodiments, other analytical techniques and/or equipment may be used to determine gas characteristics. In some embodiments, additional gas analysis devices may be included in the gas cell to detect certain gases, such as hydrogen ($H_2$), oxygen ($O_2$), and/or nitrogen ($N_2$), and some of those additional gas analysis devices may use non-optical measurement principles that do not require gas interaction with light, such as resistive, capacitive, and/or thermo-conductive sensors, by way of example.

Accurate determination of the characteristics of gas within the cavity 30 (and ultimately the dissolved gases within fluid 20) should account for contaminants and/or artifacts. Common sources of artifacts includes constituents within the air contained in the gas analysis module 24 and/or constituents within the air in the vicinity of the transformer 10 that may enter the gas analysis module 24. For example, ambient air within the gas analysis module 24 can reduce the light received by the detector 36 even though it cannot enter into the cavity 30. Accordingly, reference information regarding the ambient environment can be useful in interpreting the light received by the detector 36. In the present disclosure, the terms "air" and "ambient air" are not intended to limit the gas constituents which can be considered, but may include any gas constituent, including constituents of the same species as the dissolved gases of interest in the fluid 20. By considering such reference information of ambient air, the characteristics of the gas within the cavity 30 (and by correspondence, the characteristics of the dissolved gases within the fluid 20) can be accurately determined by correction and/or calibration of the light received by the detector 36 (absorption spectrum). Such corrective approaches can reduce the need for purging, scrubbing, desiccants, relay adjustment, and/or other resource-laden or mechanically demanding techniques to achieve accurate results.

As shown in FIG. 5, the beam 84 (split from the beam 82) illustratively propagates through a reference space 90 to provide characteristics of ambient air as reference information. The reference space 90 illustratively contains ambient gas (illustratively embodied as ambient air) which affects the beam 84 in a manner such that the affected light received by detector 38 can indicate characteristics of the ambient gas. The characteristics of the ambient gas can be used in interpreting the light received by detector 36. Analysis of the light received by the detector 36 in combination with the light received by the detector 38 can allow determination of characteristics of the gas within the cavity 30 (and, hence, the characteristics of the dissolved gases within the fluid 20) by reducing artifacts from the light absorbed by the ambient gas. Reduction of artifacts from the light absorbed by the ambient gas is illustratively achieved by consideration of the corresponding absorption spectra perceived by detectors 36, 38. In some embodiments, reference information may be obtained by any suitable technique and/or equipment.

In the illustrative embodiment as shown in FIG. 5, the beam splitter 80 effectively provides a reference source point 92 for propagation of light through the defined spaces 30, 90. The reference source point 92 is illustratively represented as a single point on the beam splitter 80 for descriptive purposes. As shown in FIG. 5, a propagation distance $d_i$ is illustratively defined between the reference source point 92 and each of the detectors 36, 38. A first propagation distance, referred to as a cell distance $d_{cell}$, is illustratively defined between the reference source point 92 and the detector 36. The cell distance $d_{cell}$ illustratively corresponds to the propagation of the beam 82. A second propagation distance, referred to as a reference distance $d_{Ref}$, is illustratively defined between the reference source point 92 and the detector 38. The reference distance $d_{Ref}$ illustratively corresponds to the propagation of the beam 84. A third propagation distance, referred to as the cell body distance L, is illustratively defined between the first window 86 and the second window 88 delimiting the cavity 30 of the gas cell 26. In the illustrative embodiment, the distance (span) resulting from the subtraction of the cell body distance L from the cell distance $d_{cell}$ (e.g., the span may include the sum of the distance between the reference source point 92 and the cavity 30, $S_1$, and the distance between the detector 36 and the cavity 30, $S_2$, as indicated in FIG. 5, either or both of which may contain ambient gas) is substantially equal to the reference distance $d_{Ref}$ in such a way that the propagation distances in ambient air between the reference source point 92 and each of the detectors 36, 38 are substantially equal. In other embodiments, however, the propagation distances in ambient air between the reference source point 92 and each of the detectors 36, 38 may be different from each other and a correlation can be applied to equate their corresponding absorption spectra.

In some embodiments, the cell distance $d_{cell}$ may be substantially equal to the sum of the reference distance $d_{Ref}$ and the cell body distance L. In some embodiments, the propagation distances between the reference source point 92 and each of the detectors 36, 38 may be substantially equal. In some embodiments, the propagation distances may be different from each other and a correlation can be applied to equate their corresponding absorption spectra.

In the illustrative embodiment, the light source 34 provides the beam of light 78 for division into beams 82, 84 for respective propagation through each of the cavity 30 and reference space 90. Thus, the light source 34 illustratively provides each of beams 82, 84 simultaneously from the same source for use in two optical channels; one channel analyzing light propagated through the gas cell 26, and another channel analyzing light propagated through the reference space 90. The dual channel arrangement using the same source of light can promote uniformity between the spectral characteristics of the channels and decrease adjustable parameters (e.g., moving optics, pressure/temperature modulation of gas samples) and/or the use of commodities (e.g., purge gas, desiccants, scrubbers) in obtaining reliable readings.

Devices, systems, and methods of the present disclosure can be advantageous for remote operation where commodities and/or maintenance availability is of concern. Moreover, arrangements of the present disclosure can account for unexpected and/or unknown contaminants, even without identifying the exact contaminant. In some embodiments, the reference information of the ambient gas may not identify one or more of the substances in the gas analysis module 24 and/or located between the light generator 72 and detectors 36, 38. However, the reference information of the unidentified substance can still be considered in accurately determining the characteristics of the gas within the cavity 30.

Figure 6:
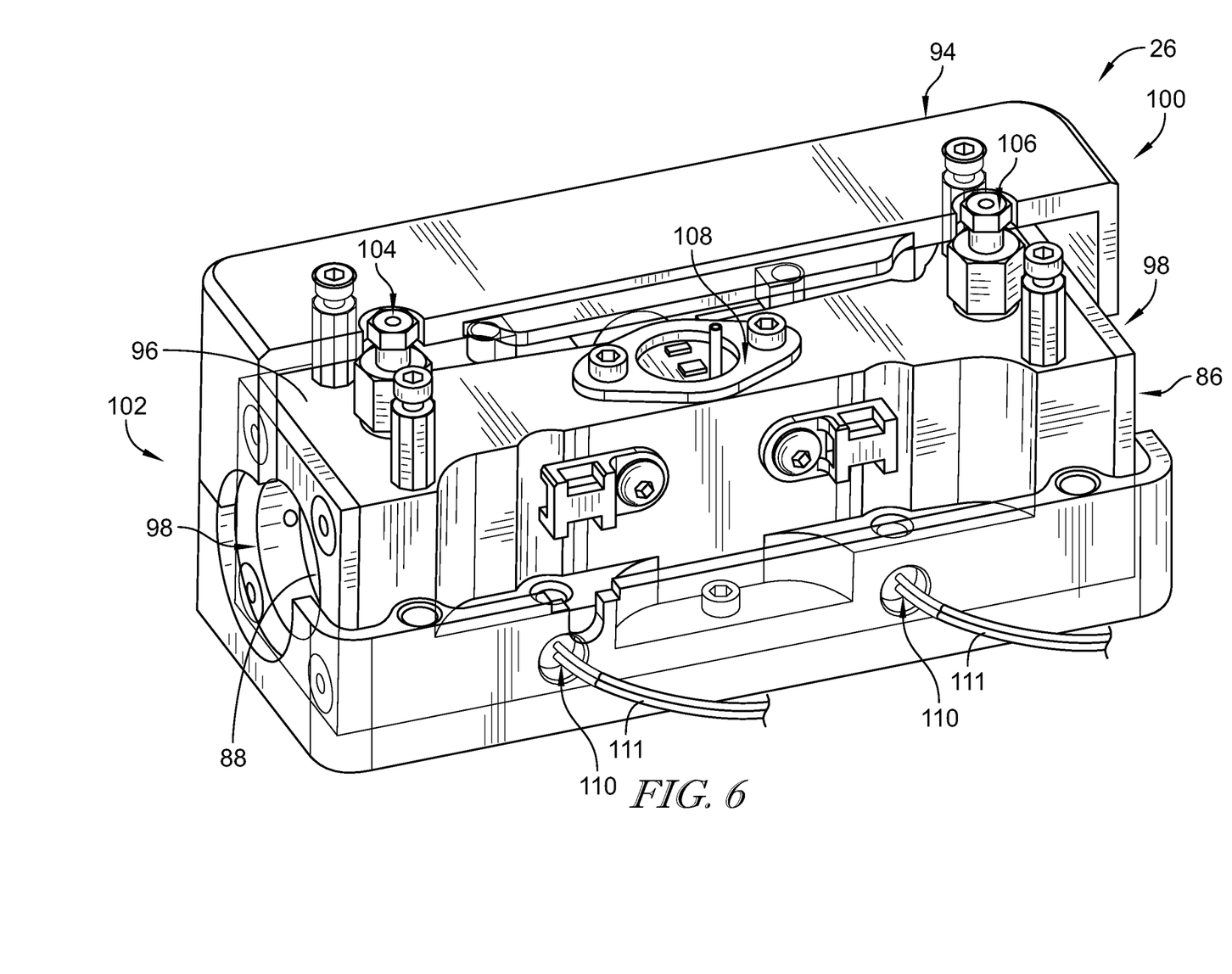
FIG. 6 is a perspective view of the gas cell of the gas analysis module showing that the gas cell includes windows for passing light.

Referring now to FIG. 6, an illustrative embodiment of the gas cell 26 is shown. The gas cell 26 illustratively includes a housing 94, which is shown partially cutaway (and semi-transparent) to reveal a cell body 96 that defines the cavity 30 therein (the cell body 96 being an illustrative embodiment of the cell body 28 of FIG. 1). The cell body 96 illustratively includes openings 98 penetrating through the cell body 96 on opposite ends 100, 102 to connect with the cavity 30. Each opening 98 is enclosed by a respective one of the windows 86, 88. The cell body 96 illustratively includes gas ports 104, 106 that each penetrate through the housing 94 and fluidly connect with the cavity 30 to form a portion of the gas circuit to communicate gas with the extraction probe 22.

The gas port 104 is illustratively embodied as an inlet port (relative to the gas cell 26) for receiving gas from the extraction probe 22 and the gas port 106 is embodied as an outlet port for sending gas to the extraction probe 22. The cell body 96 illustratively includes pressure and temperature sensor ports 108 for insertion of pressure and temperature sensors 122, 124 (shown in FIG. 1) to monitor the conditions within the cavity 30. A cell heater 110 including electrical leads 111 is illustratively connected with the cell body 96 within the housing 94 to provide temperature control of the cavity 30.

Figure 7:
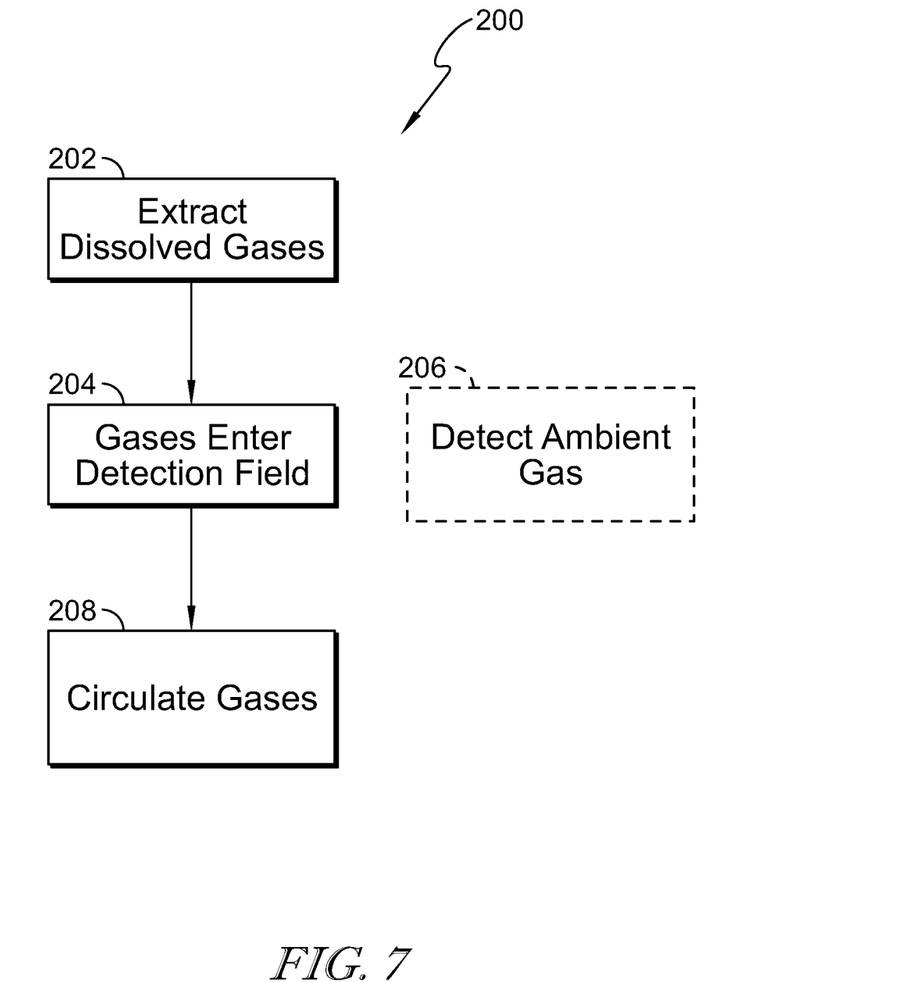
FIG. 7 is a flow diagram illustrating a process of the gas analysis system for determining characteristics of dissolved gases within fluid of the transformer.

Referring to FIG. 7, an illustrative flow diagram is shown. A process 200 for determining characteristics of gases is described relative to boxes 202-208. In box 202, dissolved gases are illustratively extracted from fluid 20 of the transformer 10. In the illustrative embodiment, the dissolved gases are extracted by permeation into the extraction probe 22 to enter the gas circuit. The process illustratively proceeds from box 202 to box 204.

In box 204, extracted gas illustratively enters a detection field. In the illustrative embodiment, the extracted gas enters the detection field as it circulates through the gas cell 26 and light is propagated through the extracted gas for reception by the detector 36. In embodiments in which reference information is used for correction, in box 206, the characteristics of ambient gases are detected. In the illustrative embodiment, the second channel of the gas analysis module 24 propagates light through the reference space 90 and the ambient gas therein for reception by the detector 38. The process proceeds from box 204 to box 208.

In box 208, gas within the detection field circulates out of the detection field. In the illustrative embodiment, gas within the gas cell 26 is circulated through the gas circuit to return to the extraction probe 22. The circulation of the gas within the gas circuit promotes non-destructive testing and enables equilibrium between gas in the gas circuit and dissolved gas within the fluid 20.

Returning briefly to FIG. 1, operation of the gas analysis system 12 and the various methods and functions described herein is illustratively governed by a control system 112. The control system 112 illustratively includes a processor 114, memory device 116, and communications circuitry 118 in communication with each other. The memory device 116 stores instructions for execution by the processor 114 to conduct operations of the gas analysis system 12. In the illustrative embodiment, the instructions include at least one algorithm for conducting the disclosed operations, but in some embodiments, the instructions may include any of look up tables, charts, and/or other reference material. The communications circuitry 118 illustratively includes various circuitry arranged to send and receive communication signals between the control system 112 and various components as directed by the processor 114. It will be appreciated that the communications circuitry 118 also allows the control system 112 to communicate with other devices, including remote devices, and along various communications networks, such that the gas analysis system 12 (as well as the transformer 10) can be connected to and form part of the Internet of Things. As a result, various components of the gas analysis system 12 may be sensed and/or controlled remotely across existing network infrastructure.

The control system 112 is illustratively arranged in communication with the gas analysis module 24 and the pump 54 through communication links 120 to communicate signals to govern their operation. Communication links 120 illustratively include hardwired connections, but in some embodiments may include any of hardwired and wireless connections, and/or combinations thereof. In the illustrative embodiment, the control system 112 is in communication with each of the light source 34, the detectors 36, 38, gas cell temperature and pressure sensors 122, 124 through individual links 120, but in some embodiments, the control system 112 may be in communication with components of the gas analysis module 24 by one or more shared links 120. The control system 112 illustratively performs spectrum analysis of the light received by the detectors 36, 38 and determines the characteristics of the gas within the cavity 30 and the corresponding characteristics of the dissolved gas within the fluid 20.

As shown in FIG. 1, the transformer 10 illustratively includes a pump 126 arranged to circulate fluid 20 within the housing 14. Circulating the fluid 20 can assist in providing uniform distribution of dissolved gases and can assist in extracted gases reaching accurate equilibrium faster than with stagnant fluid conditions. In the illustrative embodiment, the pump 126 is a thermal pump circulating the fluid 20 by convective movement. In other embodiments, any suitable device for circulating the fluid 20 may be used, including, for example, a displacement pump and/or an agitator. In the illustrative embodiment, the control system 112 is in communication with the pump 126 to govern operation of the pump 126.

In the illustrative embodiment, the control system 112 is embodied to govern operations of all components of the gas analysis system 12. In some embodiments, the control system 112 may govern operation of other systems of the transformer 10. In some embodiments, the control system 112 may include multiple processors, memory devices, and/or communications circuitry that may have any suitable arrangement including but not limited to dedicated and partly or wholly shared arrangements. In some embodiments, another control system 112 may be dedicated to govern operation of the gas analysis module 24 and the remainder of the gas analysis system 12 may be governed by the control system 112.

As mentioned above, the extraction probe 22 may include a suitable permeable material, for example, fluoropolymers. Suitable gas-permeable materials may include, for example, but without limitation, amorphous fluoroplastics. such as Teflon® AF and/or Chemours® AF, as marketed by Professional Plastics, Inc. (under affiliation and/or with permission from DuPont®), with typical properties as shown in the table below:

| Typical Properties of Teflon ® AF | |
|---|---|
| Optical Clarity | Clear: >95% |
| Upper Use Temperature, ° C. (° F.) | 285 (545) |
| Thermal Stability, ° C. (° F.) | 360 (680) |
| Thermal Expansion (linear), ppm/° C. | 80 |
| Water Absoption | No |
| Weatherability | Outstanding |
| Flame Resistant LOI, % | 95 |
| Tensile Modulus, Mpa (psi) | 950-2150 (137, 786-311, 832) |
| Creep Resistance | Good |
| Solubility | Selected solvents |
| Resistence to Chemical Attack | Excellent |
| Surface-Free Energy | Low |
| Refractive Index | 1.29-1.31 |
| Dielectric Constant | 1.89-1.93 |

Non-limiting examples may include Teflon® AF 1600 and/or Teflon® AF 2400 (and/or Chemours® AF 1600 and/or AF 2400) having typical properties as described within the table below:

| Typical Property Data for Teflon ® AF Amorphous Fluoroplastics | | | | |
|---|---|---|---|---|
| | ASTM | | Grade | |
| Property | Method | Unit | 1600 | 2400 |
| Electrical | | | | |
| Dielectric Constant | D150 | | 1.93 | 1.90 |
| Dissipation Factor | D150 | | 0.0001-0.0002 | 0.0001-0.0003 |
| Dielectric Strength | D149 | kV/0.1 mm | 2.1 | 1.9 |
| Optical | | | | |
| Optical Transmission | D1003 | % | >95 | >95 |
| Refractive Index | D542 | | 1.31 | 1.29 |
| ABBE Number | | | 92 | 113 |
| Mechanical | | | | |
| Yield Strength | | MPa | | |
| | | 23° C. (73° F.) | 27.4 ± 1.0 | 26.4 ± 1.9 |
| | | 150° C. (302° F.) | 6.7 ± 5.9 | |
| | | 220° C. (428° F.) | | 8.7 ± 4.0 |
| Tensile Strength | D638 | MPa | | |
| | | 23° C. (73° F.) | 26.9 ± 1.5 | 26.4 ± 1.9 |
| | | 150° C. (302° F.) | 7.7 ± 6.1 | |
| | | 220° C. (428° F.) | | 4.2 ± 1.8 |
| Elongation at Break | D638 | % | | |
| | | 23° C. (73° F.) | 17.1 ± 5.0 | 7.9 ± 2.3 |
| | | 150° C. (302° F.) | 89.3 ± 13.1 | |
| | | 220° C. (428° F.) | | 8.4 ± 4.1 |
| Tensile Modulus | D638 | GPa | 1.6 | 1.5 |
| Flexural Modulus | D790 | GPa | | |
| | | 23° C. (73° F.) | 1.8 ± 0.1 | 1.6 ± 0.1 |
| | | 150° C. (302° F.) | 1.0 ± 0.1 | |
| | | 220° C. (428° F.) | | 0.7 ± 0.1 |

Typical Property Data for Teflon ® AF Amorphous Fluoroplastics

| Property | ASTM Method | Unit | Grade 1600 | Grade 2400 |
|---|---|---|---|---|
| Hardness | | | | |
| Rockwell | D785 | 23° C. (73° F.) | 103 | 97.5 |
| Durometer | D1706 | Shore D | | |
| | | 23° C. (73° F.) | 77 | 75 |
| | | 150° C. (302° F.) | | |
| | | 220° C. (428° F.) | 70 | 65 |
| Impact Strength | Notched Izod | N | — | — |
| Deflection Temperature | D648 | ° C. (° F.) | | |
| (66 psi) | | | 156 (313) | 200 (392) |
| (264 psi) | | | 154 (309) | 174 (345) |
| Chemical | | | | |
| Contact Angle with Water | D570 | Degrees | 104 | 105 |
| Critical Surface Energy | | Dynes/cm | 15.7 | 15.6 |
| Taber Abrasion | | cc/2000 cycles | 0.107 | 0.2 |
| Chemical Resistance | | | | |
| Water Absorption | | % | <0.01 | <0.01 |
| Gas Permeablity | | | | |
| $H_2O$ | | Barrer | 1142 | 4026 |
| $O_2$ | | Barrer | 340 | 990 |
| $N_2$ | | Barrer | 130 | 490 |
| $CO_2$ | | Barrer | | 2800 |
| Other | | | | |
| $T_g$ | D3418 | ° C. (° F.) | 160 (320) ± 5 | 240 (464) ± 10 |
| Specific Gravity | D792 | | 1.78 | 1.67 |
| Melt Viscosity | D3835 | Pa s | 2657 at 250° C. 100 $s^{-1}$ | 540 at 350° C. 100 $s^{-1}$ |
| Volume Coefficient of Thermal Expansion | E831 | ppm/° C. | 260 | 3011 |

In some embodiments, any suitable materials for gas-permeable, liquid-resistant extraction of dissolved gases from transformer fluid may be applied.

The present disclosure includes devices, systems, and methods for oil and gas management for dissolved gas analyzers for use in transformer monitoring. The devices, systems, and methods of the present disclosure may include detecting dissolved gases in insulating oil of electrical equipment using gas equilibrium theory. Equilibrium can be achieved relative to the solubility of a gas in a transformer fluid 20, such as mineral oils, ester-based oils, or other insulation fluids, at a given temperature and for a given partial vapor pressure of a gas. Gas solubility can be described with quantities such as Ostwald coefficients of gas solubility that are specific to the type of fluid and to each gas constituent and may have temperature dependency. Gas solubility coefficients can be used to relate the partial pressure of gas in the gas cell with the concentration of dissolved gas in oil. The extracted gases being in equilibrium with the dissolved gases in oil may provide more accurate readings without requiring precise knowledge of extraction rates. In some embodiments, the extraction probe 22 of the present disclosure may comprise at least one ring of highly gas permeable tubing that is not permeable to liquid. In some embodiments, the extraction probe 22 may be connected to a closed-circulation system. The closed-circulation system may include one or more pumps for gas circulation and a gas cell, for example, gas cell 26, for analytical measurement of the gas.

The present disclosure includes devices, systems, and methods adapted to monitor the health of a transformer by measuring dissolved gases within insulating oil of the transformer. For example, the concentration of specific gases can give indications of specific aspects of the operation of the transformer. Direct oil sampling and analysis of dissolved gases contained in transformer oil use active extraction of the gases and active measurement technics that consume the gases through the analyses. They are often implemented by circulating and/or conditioning oil samples outside the transformer in an oil circuit and may present a risk of oil leakage in case of breakage of the oil circuit. By contrast, embodiments of the devices, systems, and methods of the present disclosure permit online measurement with high accuracy and without active extraction. In some of the disclosed embodiments, oil containing the dissolved gases is circulating around highly permeable material tube within a fluid chamber 46 communicating fluidly with the transformer 10 through the pipe extension 42. In some embodiments, the oil circulation around the permeable tube may be generated by pump, propeller and/or other mechanical systems and/or using thermally induced convection. Gases contained in oil can pass through permeable material to reach the gas phase loop. The permeable material properties can assist in obtaining equilibrium between gases in the liquid and gases in the gas phase loop. The gas loop may include a gas cell with optical inlet and outlet allowing examination of the gases by optical analyzer.

Devices, systems, and methods of the present disclosure may include highly permeable fluoropolymer tubing, such as Teflon AF family of amorphous fluoroplastics, by way of example. Highly gas permeable material can promote gas equilibrium and can improve measurement response time.

The tubing may be rolled to form one or more turns of a coil. Devices, systems, and methods of the present disclosure may include circulation of the transformer fluid (e.g., oil) around this coil. A structural ring may support the tubing. According to the present disclosure, the fluoropolymer tubing may be connected to a gas circulating loop. The gas circulating loop may include one or more pumps to enhance reliability. In some embodiments, stainless steel tubing may transport gas to a gas cell for analysis. In some embodiments, a spectrometer may perform analysis of the gases. In some embodiments, in-oil sensors may be used for $H_2$ and/or $H_2O$ measurement.

Devices, systems, and methods of the present disclosure may include passive extraction of dissolved gases and measurement, in lieu of active principles for gas separation and measurement. In some embodiments, the present disclosure may include transport of extracted gases without a carrier medium (e.g., a carrier gas). In some embodiments, a lower pressure may be formed within the extraction probe 22, relative to the pressure within the gas cell 26 to assist with extraction of dissolved gases.

Devices, systems, and methods of the present disclosure can be used in transformer monitoring and/or specifically in monitoring of dissolved gases analysis in transformer fluid such as oil. For gas phase analysis, gases can be extracted from the transformer oil. Measurement of the gases can require a complex system for analysis, and in some embodiments, the gas sample can be transported to a gas analyzer. The devices, systems, and methods of the present disclosure can be helpful in avoiding transporting the transformer oil itself to an analyzer, which can present a risk of oil leakage in case of tubing breakage.

Use of passive measurement and passive extraction of the gases can simplify the calibration and installation of gas analysis systems. Use of high porosity and/or highly permeability material can help to reach equilibrium between gases in oil and gases in the sample gas phase. Using gases equilibrium, without requiring new gases to be sampled, can reduce risk of contamination of the oil. Use of a lower pressure (relative to the pressure within the gas cell) in the gas sampling probe can reduce the response time of the systems. The use of multiple transport pumps can help to reduce risk of failure. In some embodiments, measurement of $H_2$ may be conducted in gas phase to reduce the cost. In some embodiments, measurement of $O_2$, $H_2$, and/or $N_2$ may be performed optically and/or with non-optical sensors. In some embodiments, $O_2$ can be measured by paramagnetic analyzer. In some embodiments, gas leak detection may be performed by monitoring the presence of $CO_2$ or $H_2O$ with the gas cell, whether by direct and/or indirect sampling. The present disclosed devices, systems, and methods may involve advanced analyses and identification of interferent and outlier.

The present disclosure includes devices, systems, and methods for dual channel optical gas analyzers for compensation of ambient air constituents. Spectrometers can be used to measure light absorption spectra of gases. When gases of interest in a sample under observation are also present in ambient air (e.g., air either in the analyzer and/or around the sampling system) or when other gases in ambient air might interfere with the measurement of the gases of interest, spectrometers often must be purged, for example, with a purified gas to determine the contribution due to the absorption of only the gases of interest in the gas sample. The present disclosure includes devices, systems, and methods to reduce and/or remove the need for conditioning of the air in the analyzer or around the sampling system. The present disclosure includes spectrometers with two measurement channels. One channel can receive light propagating through ambient air and through a sampling gas cell. The transmitted light is then detected by a photodetector which generates an electrical signal that is digitized using an analog to digital converter. Another channel receives light propagating through ambient air only. Unlike in the first channel, the light of this second channel is not propagating through the sampling gas cell. The gas absorption contribution to the transmitted light in this second channel is related to ambient air constituents. The transmitted light of this second channel is detected by a second photodetector which generates an electrical signal that is digitized using a second analog to digital converter.

Devices, systems, and methods within the present disclosure may include light sources that split the light (e.g., by beam splitter, light divider, and/or any other suitable light splitting technique), a gas cell that may contain one or many gases of interest, components to insert gases into the gas cell, a first detector measuring the light transmitted through the gas cell and through ambient air, a second detector measuring the light transmitted only through ambient air, a processor to determine the concentration of one or more gases present in the sampling gas cell from the first channel signal, and remove interferences and/or contribution of gases in ambient air of the first channel based on the ambient air signal recorded from the second channel.

In some embodiments, a light source may be modulated by an interferometer. The light source may be divided in two different beams by a 50/50 Wedged ZnSe Beamsplitter. One of the beams may propagate through the gas cell and may reach the gas cell detector. The other beam may be directed towards a reference detector, to sense the ambient air composition only. The propagation distance in ambient air can be adjusted for both beams. The adjustment can be performed in a manner such that both the light transmitted by the gas cell and reaching the first detector and the light reaching the reference detector of the second channel propagate through similar distances in ambient air. In some embodiments, it may be assumed that ambient air composition in the instrument is homogeneous, and the light absorption due to the gases from ambient air should be the proportional to the gases concentration as well as to the respective propagation distance of both channels.

In some embodiments, the gas cell may be a closed container with one inlet and one outlet to fluidly connect to form a gas circulation loop. The light from the interferometer can enter the gas cell from one side and exit through the other side to the gas cell detector. The gas cell can be temperature controlled by a cartridge heater. The pressure and temperature of the gases in the gas cell can be measured and used as input parameters to the calculation of gases concentrations.

The present disclosure includes devices, systems, and methods in which the need for a purging system can be reduced and/or removed. Reducing and/or removing the need for a purging system can be an advantage when an analyzer is located in remote areas and purging systems are not available and/or are costly to install and operate. Concentration of gases in the gas cell that may also be present ambient air can be determined without purge, scrubber, desiccant and/or analyzer sealing. Other ambient air gases which have absorption signatures that may interfere with the determination of the gases concentration in the gas cell may also be compensated without purge, scrubber, desiccant and/or sealing. With the teachings of the present disclosure, the gases in ambient air can be measured simultaneously with the gases in the gas cell if desired, as opposed to calibration methods where only one channel can be used. Single channel calibration may perform reference background measurement taken apart from and/or without the gases of interest in the gas cell. The devices, systems, and methods of the present disclosure can provide an advantage when ambient air composition varies over time. The devices, systems, and methods of the present disclosure can include calibration for spectral intensity of the source, and calibration for the spectral characteristics of optical components that are common to both the first and second channels.

The present disclosure can be used in the field of transformer monitoring by analysis of dissolved gases. The teachings of the present disclosure are generally applicable to other fields where optical methods require purge, scrubber, desiccant and/or sealing in order to calibrate, remove, and/or correct for ambient air constituents. The devices, systems, and methods of the present disclosure can provide an alternative to systems taking reference measurements using only one detector, by removing the gases of interests from the gas cell and/or bypassing the gas cell.

Measuring low concentration gases by spectroscopy with accuracy can be challenging, particularly when the same gases or other interfering gases are present in ambient air, either in the analyzer or around the sampling system. Concentration of these gases in ambient air and/or the relative propagation distance of the light in ambient air could be non-negligible compared to the concentration of the gases in the gas cell and the propagation distance in the gas cell. Furthermore, the concentration of these gases in ambient air may vary with time, and unexpected gases can appear in ambient air in some sites. Pressure and temperature of the ambient air may differ from the pressure and temperature of the gas sample in the gas cell.

To remove the contribution of ambient air gases, analyzers are often purged with purified gases (by way of example, the MB3000 spectrometer marketed by ABB Inc., includes a purging option). Purging can require bottles of purified gases, like Nitrogen, and/or a purified gas generator. Purge air is often dried to remove humidity, which can be a significant interferent in some instances, and $CO_2$ is often removed as well with a scrubber. In other systems where a purge is not possible and/or desirable, desiccants and/or scrubbers are used to remove humidity and/or other gases, but must be replaced or regenerated after some time. Other exemplary techniques can include moving relay mirrors to the gas cell in and out of the first channel in order to bypass the gas cell and direct the light to the detector to take background measurement. The relay optics can be designed such that the propagating distance in air with and without the relay optics is the same. Still other exemplary techniques can include using a scrubber to remove the gas component of interest from the gas cell after measuring the gas sample with the gas component of interest and inferring its concentration by the comparison of those two alternate measurements. Still other techniques may vary the pressure and/or the temperature of the gas sample to discriminate its composition over ambient air composition. In cases where the purge gas is supplied from an exhaustible source, such as a bottle, the exhaustible source will need to be refilled and/or changed at periodic maintenance intervals. Purge generators can be costly equipment that can require maintenance as well. Scrubbers and desiccants also require maintenance. Thus, the purge-based systems can increase the cost of operating spectrometers.

As mentioned above, the present disclosure can include reducing and/or removing the need for a purging system, desiccants, scrubbers and/or instrument sealing. Accordingly, the devices, systems, and methods of the present disclosure can reduce installation and/or maintenance costs related to the spectrometer, and can enable solutions for remote sites where purging systems are not available and/or maintenance cannot be performed frequently due to cost and/or safety issues. In some embodiments, the devices, systems, and methods of the present disclosure do not require moving optics and/or sample gas pressure modulation, and the ambient air constituents can be measured simultaneously with the gas cell constituents.

Since spectrometers using certain teachings of the present disclosure can measure spectra of ambient air, they may also detect and/or compensate for unexpected gases present in the ambient air, as opposed to scrubbers that are designed for specific constituents. Devices, systems, and methods of the present disclosure may be used to detect other defects around the transformer, for example but without limitation, detection of insulation gas leaks, such as $SF_6$. By measuring and removing ambient air absorption, the devices, systems, and methods of the present disclosure can reduce sensitivity to ambient air compositions. The composition of the air inside the optical analyzer and/or around the sampling system may not need to be controlled by use of purge system, desiccants, scrubbers and/or instrument sealing.

In some embodiments, the devices, systems, and methods of the present disclosure may use factory calibration to characterize the difference of light propagating distances in air between first and second channels. In some embodiments, the devices, systems, and methods of the present disclosure may use factory calibration of the system to measure the spectral response of the first and second detectors as well as spectral response of optical components not common to first and second channel. In some embodiments, the devices, systems, and methods of the present disclosure may use factory calibration to characterize the spectral response and/or instrument line shape of the first and second channels in order to improve the compensation of air constituents in the first channel using the second channel. Factory calibration may include purge of the analyzer. The present disclosure include techniques developed to adjust the position of system components (mirrors, lenses, detectors, etc.) to minimize the difference of light propagating distance in air between first and second channel. In some embodiments, one or more algorithms may be used to compensate for the ambient air constituents of the first channel using the second channel signal.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the methods, systems, and articles described herein. It will be noted that alternative embodiments of the methods, systems, and articles of the present disclosure may not include all of the features described yet still benefit from at least some of the advantages of such features. Those of ordinary skill in the art may readily devise their own implementations of the methods, systems, and articles that incorporate one or more of the features of the present disclosure.

The invention claimed is:

1. A gas analysis system for determining characteristics of gas dissolved in a fluid of a transformer, the system comprising:
   an extraction coil for contact with the fluid, the extraction coil including gas- permeable material for receiving dissolved gas,
   a gas analyzer for determining gas characteristics, the gas analyzer including a gas cell having a cavity for receiving gas for analysis, and
   a gas circuit formed to include the extraction coil and the gas analyzer to circulate gas.

2. The gas analysis system of claim 1, wherein the extraction coil includes a number of coil loops each permitting dissolved gas to permeate therein.

3. The gas analysis system of claim 1, wherein the gas circuit includes a transport conduit fluidly coupled with each of the extraction coil and the gas analyzer to transport gas between the extraction coil and the gas cell for analysis.

4. The gas analysis system of claim 3, wherein the transport conduit includes a motive pressure source fluidly coupled with the extraction coil to circulate gas through the transport conduit.

5. The gas analysis system of claim 4, wherein the motive pressure source is fluidly coupled with the extraction coil to provide a lower pressure within the extraction coil relative to a pressure within the cavity of the gas cell.

6. The gas analysis system of claim 3, wherein the transport conduit includes a supply segment fluidly connected to provide gas from the extraction coil to the gas cell and a return segment fluidly connected to provide gas from the gas cell to the extraction coil.

7. The gas analysis system of claim 1, wherein the gas analyzer includes a light source and at least one light detector for receiving light from the light source.

8. The gas analysis system of claim 7, wherein the light source is arranged to pass light from one side of the gas cell through gas within the cavity of the gas cell to another side of the gas cell, and the at least one light detector is arranged on the another side to receive light from the light source.

9. The gas analysis system of claim 1, wherein the cavity of the gas cell is for receiving dissolved gas extracted from the fluid.

10. The gas analysis system of claim 1, wherein the gas-permeable material includes a fluoropolymer.

11. The gas analysis system of claim 10, wherein the gas-permeable material includes a fluoroplastic having at least one of: a yield strength within the range of about 26 MPa to about 29 MPa at about 73° F., a yield strength within the range of about 0.5 MPa to about 13 MPa at about 302° F., a yield strength within the range of about 4 MPa to about 13 MPa at about 428° F., a tensile strength within the range of about 24 MPa to about 29 MPa at about 73° F., a tensile strength within the range of about 1 MPa to about 15 MPa at about 302° F., and a tensile strength within the range of about 3 MPa to about 7 MPa at about 428° F.

12. The gas analysis system of claim 1, wherein the extraction coil is formed as a conduit having an inner volume for receiving gas permeating through the gas-permeable material.

13. The gas analysis system of claim 12, wherein a gas species that is both within the inner volume and dissolved in the fluid is in equilibrium.

14. The gas analysis system of claim 3, wherein the transport conduit is fluidly coupled with the cavity of the gas cell to provide gas for analysis.

15. The gas analysis system of claim 3, wherein the transport conduit is fluidly coupled with an inner volume of the extraction coil for circulating gas.

16. The gas analysis system of claim 1, wherein the gas cell includes at least one gas port for communicating gas via a transport conduit of the gas circuit.

17. The gas analysis system of claim 16, wherein the at least one gas port includes at least one inlet port for communicating gas from the transport conduit of the gas circuit and at least one outlet port for communicating gas to the transport conduit of the gas circuit.

18. The gas analysis system of claim 17, wherein the at least one inlet port is arranged near a first end of the gas cell and the at least one outlet port is arranged near a second end of the gas cell.

19. The gas analysis system of claim 18, wherein the first and second ends of the gas cell are opposite each other.

20. The gas analysis system of claim 18, wherein the gas analyzer includes a light source arranged to pass light between the first and second ends of the gas cell.

* * * * *